US009700590B2

(12) United States Patent
Romero et al.

(10) Patent No.: US 9,700,590 B2
(45) Date of Patent: Jul. 11, 2017

(54) METHODS AND MATERIALS FOR REDUCING OR ELIMINATING RISK FACTORS ASSOCIATED WITH SYNDROME X

(75) Inventors: Timothy Romero, Sarasota, FL (US); Peter Miller, Broomfield, CO (US)

(73) Assignee: IN Ingredients, Inc., Columbia, TN (US)

(*) Notice: Subject to any disclaimer, the term of this patent is extended or adjusted under 35 U.S.C. 154(b) by 376 days.

(21) Appl. No.: 12/917,626

(22) Filed: Nov. 2, 2010

(65) Prior Publication Data

US 2011/0052736 A1    Mar. 3, 2011

Related U.S. Application Data

(63) Continuation-in-part of application No. 11/182,701, filed on Jul. 15, 2005, which is a continuation-in-part of application No. 11/735,516, filed on Apr. 16, 2007, now abandoned, which is a continuation-in-part of application No. 11/673,063, filed on Feb. 9, 2007, now abandoned, which is a continuation-in-part of application No. 10/905,142, filed on Dec. 17, 2004, now abandoned.

(60) Provisional application No. 60/521,157, filed on Mar. 1, 2004, provisional application No. 60/521,885, filed on Jul. 16, 2004.

(51) Int. Cl.
*A61K 36/54* (2006.01)
*A23L 33/105* (2016.01)

(52) U.S. Cl.
CPC ............ *A61K 36/54* (2013.01); *A23L 33/105* (2016.08); *A23V 2002/00* (2013.01)

(58) Field of Classification Search
None
See application file for complete search history.

(56) References Cited

U.S. PATENT DOCUMENTS

| 6,200,569 B1 | 3/2001 | Cheng et al. |
| 6,967,030 B2 | 11/2005 | Wright et al. |
| 7,125,573 B2 | 10/2006 | Okawa et al. |
| 2004/0224035 A1 | 11/2004 | Miller et al. |

FOREIGN PATENT DOCUMENTS

| CN | 1366986 A | * | 9/2002 | |
| JP | 358129002 A | | 8/1983 | |
| JP | 2002179586 A | * | 6/2002 | |
| JP | EP 1350516 A1 | * | 10/2003 | ............... A21D 2/36 |
| WO | WO 9922752 A1 | * | 5/1999 | |

OTHER PUBLICATIONS

"Hyperglycemia (High blood glucose)" in American Diabetes Association. Copyright 1995-2012 [Retrieved from the Internet on: Mar. 14, 2012]. Retrieved from the Internet: <URL: http://www.diabetes.org/living-with-diabetes/treatment-and-care/blood-glucose-control/hyperglycemia.html?print=t>.*
"Medications for treating hypertension" in Harvard Health Publications: Harvard Medical School (2009). Retrieved from the Internet on: Mar. 14, 2012. Retrieved from the Internet: <URL: http://www.health.harvard.edu/newsletters/Harvard_Womens_Health_Watch/2009/August/Medications-for-treating-hypertension?print=1>.*
"Our care: Pre-Diabetes (Hyperglycemia)". Retrieved from the Internet on: Sep. 14, 2012. Retrieved from: <URL: http://patients.dartmouth-hitchcock.org/endo/pre-diabetes.html>.*
Michael Blaha et al.; Clinical Use of the Metabolic Syndrome: Why the Confusion?; Clinical Diabetes http://clinical.diabetesjournals.org; (2006); pp. 1-15.
Kannappan S. et al.; Cinnamon Bark Extract Improves Glucose Metabolism and Lipid Profile in the Fructose-Fed Rat; Singapore Med J.; (2006); pp. 858-863.
Donald M. Cohen et al.; Cinnamon-Induced Oral Erythema Multiformelike Sensitivity Reaction; Clinical Practice; Jada, vol. 131. Jul. 2000; pp. 929-934; American Dental Association.
Tim N. Ziegenfuss; Effects of a Water-Soluble Cinnamon Extract on Body Composition and Features of the Metabolic Syndrome in Pre-Diabetic Men and Women; pp. 1-20.
Mark C. Houston et al.; Metabolic Syndrome Contributing Factors; The Journal of the American Nutraceutical Association; Jana vol. 8, No. 2 (2005); ISSN—1521-4524; pp. 1-85.
Wikipedia Encyclopedia; Polyphenol; <http://en.wikipedia.org/wiki/Polyphenol>; <http://en.wikipedia.org/wiki/Phenol>; <http://en.wikipedia.org/wiki/Chalcone>; pp. 1-3.
Karalee J. Jarvill-Taylor et al.; A Hydroxychalcone Derived From Cinnamon Functions as a Mimetic for Insulin in 3T3-L1 Adipocytes; Journal of the American College of Nutrition, vol. 20, No. 4, pp. 327-336 (2001).
Wikipedia Encyclopedia; Catechin; <http://en.wikipedia.org/wiki/Catechin; pp. 1-2.
About.com; Metabolic Syndrome X; URL <http://heartdisease.about.com/cs/cholesterol/a/metsynx.htm> accessed Feb. 13, 2006.
Kahn, A., et al. Cinnamon Improves Glucose and Lipids of People With Type 2 Diabetes: Diabetes Care; Dec. 2003; 26, 12, pp. 3215-3218.
Coghlan, A. Sugar and Spice; New Scientist, Aug. 12, 2000; vol. 167, No. 2251, p. 1-2 (one page from STN database printout.).
Grundy, S. Does the Metabolic Syndrome Exist?; Diabetes Care, Jul. 2006, vol. 29, Issue 7, p. 1689, 4 pages (pages 1-5 of ProQuest print-out).

(Continued)

*Primary Examiner* — Amy L Clark
(74) *Attorney, Agent, or Firm* — Dinsmore & Shohl LLP

(57) ABSTRACT

A composition containing cinnamon extract reduces and/or eliminates one or more risk factors associated with Syndrome X. The composition also includes optionally one of more components selected from the group consisting of vitamins, cholesterol lowering agents, lipid lowering agents, and glucose lowering agent. Also described is a method of reducing and/or eliminating risk factors associated with Syndrome X in a subject through the administration of the cinnamon extract. The cinnamon extract supplement is administered orally, intravenously, or subcutaneously. In one embodiment, a daily dose of 10-1,000 mg of the cinnamon extract supplement is administered to the subject for a period of 6 weeks to 6 months.

7 Claims, 2 Drawing Sheets

(56) References Cited

OTHER PUBLICATIONS

Wikipedia Encyclopedia; Phenol; http://en.wikipedia.org/wiki/Phenol.
Wikipedia Encyclopedia; Chalcone; http://en.wikipedia.org/wiki/Chalcone.
About.com; Metabolic Synrome X; URL <http://heartdisease.about.com/cs/cholesterol/a/metsynx.htm> accessed Feb. 13, 2006.
Alam Khan et al., Cinnamon Improves Glucose and Lipids of People With Type 2 Diabetes; Diabetes Care, vol. 26, No. 12, Dec. 2003.
MacPhillam: Drugs From Plants; Plant Science Bulletin; A publication of the Botanical Society of America, Inc. vol. 9, Apr. 1963, No. 2, pp. 1-15 as retrieved from online URL <http://www.botany.org/PlantScienceBulletin/psb-1963-9-2 php>.
Raskin et al: Can an Apple a Day Keep the Doctor Away? Current Pharmaceutical Design, 2004,10, pp. 3419-3429.
Winter; Functional Foods & Nutraceuticals; Jan 2006; p. 42.
Ziegenfuss et al; Effects of a Water-Soluble Cinnamon Extract on Body Composition and Features of the Metabolic Syndrome in Pre-Diabetic Men and Women; Journal of the International Society of Sports Nutrition; A National Library of Congress Indexed Journal; ISSN #1550-2783; pp. 45-53.

* cited by examiner

METHODS AND MATERIALS FOR REDUCING OR ELIMINATING RISK FACTORS ASSOCIATED WITH SYNDROME X

REFERENCE TO RELATED APPLICATIONS

This application is a continuation-in-part of and claims priority of: U.S. patent application Ser. No. 11/182,701, filed Jul. 15, 2005, which claims priority of U.S. Provisional Application 60/521,885 filed Jul. 16, 2004; and a continuation-in-part and claims priority of U.S. patent application Ser. No. 11/735,516 filed Apr. 16, 2007, which is a continuation-in-part of U.S. patent application Ser. No. 11/673,063 filed Feb. 9, 2007 which in turn is a continuation-in-part of U.S. patent application Ser. No. 10/905,142, filed Dec. 17, 2004, which claims priority of U.S. Provisional Patent Application Ser. No. 60/521,157 filed Mar. 1, 2004. The contents of each of these parent applications are incorporated herein by reference in their entirety.

FIELD OF THE INVENTION

The present invention generally relates to the use of cinnamon extract as a preventive, alleviative or remedy for reducing risk factors associated with Syndrome X, and in particular to reducing systolic blood pressure, fasting blood glucose, or percentage of body fat in a subject with Syndrome X.

BACKGROUND OF THE INVENTION

Syndrome X is a metabolic condition characterized by the presence of several of the following risk factors: hyperglycemia, hypertension, low high-density lipoprotein (HDL), high low-density lipoprotein (LDL), high triglyceride, and abnormal body mass index (BMI), micro-albuminuria, endothelial dysfunction, pro-thrombotic state, and inflammatory process. Although not all these criteria need to be met before a diagnosis of the disease may be found. In fact, three occurrences of these symptoms may be found indicative of the disease.

It is estimated that over 22% of the adult U.S. population have Syndrome X and the incidence is rapidly increasing each year. Old age, postmenopausal status, ethnicity, higher body mass index, current smoking, low household income, high carbohydrate intake, and physical inactivity all have been connected with the increased odds of the onset and or deterioration of Syndrome X. An additional 12 million adults will likely develop the condition as a result of aging alone by 2022.

Not a single cause at the molecular level can be traced to the origin of Syndrome X. However, increasing evidence suggests the condition originates from both insulin resistance and activation of vascular inflammatory mechanisms related to increased oxidative stress. For example, insulin resistance results in preferential metabolism of free fatty acids which leads to reduced glucose utilization. Insulin resistance is identified in children prior to the development of the dyslipidemia, hypertension and hyperglycemia that occur later in life. As one ages, pancreatic beta cell exhaustion is not able to meet insulin resistance demands, and this might eventually lead to the progression of metabolic disturbance including dyslipidemia, hypertension, etc. On the other hand, the infiltration of adipose tissue by inflammatory macrophages has been indicated as a common feature of obesity. Adipose mass correlates quantitatively with genetic expression of macrophages that produce inflammatory mediators and markers. Therefore, while Syndrome X may share some characteristic features with diabetes, it is not a diabetic or pre-diabetic condition per se. Other distinct factors and causes are also involved.

All in all, the treatment for Syndrome X varies greatly. Many times, a person diagnosed with several risk factors as discussed above would be prescribed a low fat diet, exercise regime, and pharmaceutical intervention including a host of drugs to individually combat issues with cholesterol, blood pressure, glucose, and body weight. Due to the complicated nature of such therapy, often times compliance is rather low.

Cinnamon is known in the art for the control of blood glucose. Broadhurst et al. demonstrated that cinnamon is a strong potentiator of insulin in comparison to various other herbs and spices (J. Agric. Food Chem., 2000; 48:849-852). Researchers have demonstrated that cinnamon's glucose-lowering effects are from a class of compounds other than chromium. One study by Kahn et al. compared the chromium levels of foods and spices including cinnamon, and failed to find a correlation between chromium level and the level of insulin potentiation (Biological Trace Element Research, 1990; 24: 183-188). A meta-analysis by Althuis et al. showed no association between chromium and glucose or insulin concentration (Am. J. Clin. Nutr., 2002; 76: 148-55).

In a more recent study by Khan et al. (Diabetes Care, 2003, 26, 3215-3218), type II diabetes patients were found to have their glucose and lipid profile improved after cinnamon intake. These patients were of age 40 and above with glucose levels in the range of 140-400 mg/dL. Daily treatment with cinnamon reduced fasting glucose levels by 18-29% in these patients, as well as triglycerides by 23-30% and LDL by 7-27%. It is noted that these patient were "very diabetic" when recruited for the study. Although rendered "less diabetic" after the cinnamon treatment, these patient were still diabetic with abnormally high blood glucose levels. So it remains to be determined whether the raw cinnamon regime as prescribed in this study would be effective to reverse these patients' glucose level from an abnormal state to a normal state, as defined by NCEP-ATP-III. In addition, another important biomedical parameter, lean body mass, was not examined in this study.

Therefore, and in view of the fact that Syndrome X is distinguishable in cause and effect from diabetes, these prior art disclosures do not teach a treatment for pathological states such as hypertension and hyperglycemia in subjects who are not already diabetic; nor do they support a method to concurrently reduce and improve three or more risk factors associated with the Syndrome X even in diabetic subjects. Furthermore, these prior art documents fail to provide a useful teaching on how to eliminate a risk factor or reverse a disease state, for example, to render the subject from being diabetic to non-diabetic.

To date, the prior art has not provided any therapeutic materials which can specifically address Syndrome X. Heretofore, therapies have been directed to the treatment of specific features of the syndrome on an individual basis, and not to any holistic therapy. As will be explained in detail, the present invention recognizes that particular cinnamon-derived materials are effective in simultaneously controlling multiple pathologies of Syndrome X. Furthermore, the therapeutic materials and methods hereof are simple to implement and conducive to good patient compliance.

SUMMARY OF THE INVENTION

The present invention relates to a composition containing a cinnamon extract and a method of using the composition to prevent, alleviate, and treat risk factors associated with Syndrome X in a subject. In particular instances, the subject is non-diabetic, and in certain instances the subject is pre-diabetic. In some instances the composition contains a known concentration of at least one active component such as a polyphenol A, and it is to be understood that such polyphenols include, but are not limited to, type A polymers and oligomers.

DETAILED DESCRIPTION OF EMBODIMENTS OF THE INVENTION

Figure 1:
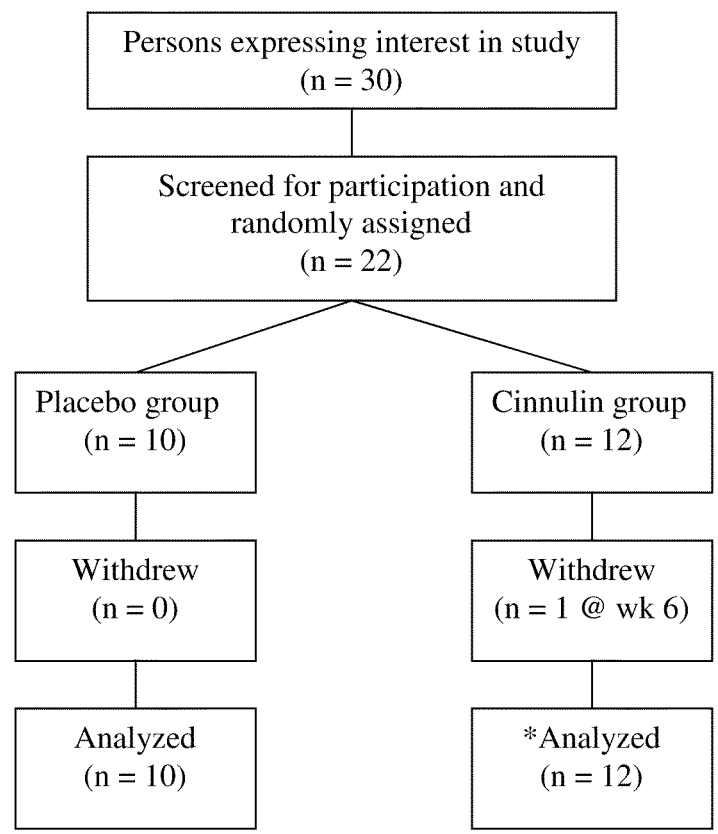
FIG. 1 depicts a flowchart for the study examining effects of a water-soluble cinnamon extract on features of the Syndrome X in pre-diabetic men and women.

The following description of several embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. The invention provides materials in the form of botanical extracts, such as extracts of cinnamon, that have utility for altering a risk factor of Syndrome X in subjects that are diabetic or pre-diabetic.

"Risk factor" is a pathological disorder that contributes to the formation of a diagnostic Syndrome X. Illustrative risk factors include: abnormal systolic blood pressure; abnormal fasting blood glucose; abnormal body mass index; abnormal high-density lipoprotein; abnormal low-density lipoprotein; abnormal very-low density lipoprotein; abnormal blood triglyceride; abnormal central obesity; and abnormal body mass index. A risk factor is optionally reduced by increasing or decreasing the measured parameter depending on the level of the risk factor relative to a desired level. Optionally, HDL levels or lean muscle mass are increased, while LDL levels, triglyceride levels, obesity, and blood pressure are optionally decreased.

"Polyphenol" refers to a group of chemical substances found in plants, characterized by the presence of more than one phenol group per molecule. For purposes of this disclosure, it is to be understood that polyphenols include, but are not limited to, type A polymers and oligomers or phenolic materials. Research indicates that a class of polyphenol has antioxidant characteristics with potential health benefits. Sources of polyphenols include green tea, white tea, red wine, dark chocolate, olive oil, and other fruits, vegetables, and plants including cinnamon.

"Polyphenol Type-A polymers" are the bioactive type of polymers in the cinnamon extract. They are identified by their protonated molecular masses as A type doubly linked procyanidin oligomers of the catechins and/or epicatechins. The polymers are composed of monomeric units.

"Reducing" a risk factor relates to a change in the risk factor that moves the risk factor more toward a desired level. Thus, a risk factor is optionally reduced when the risk associated with the factor is reduced. Illustratively, when fasting blood glucose is reduced, the risk factor is therefore reduced. Similarly, when lean mass or HDL levels are increased, the risk factor is reduced. A risk factor reduction is optionally statistically significant with p-value<=0.05; however, it does not need to render the risk factor absent or satisfactory according the criteria recognized by common medical practices. One particular criteria is established by NCEP-ATP-III.

"Eliminating" a risk factor means that the risk factor is rendered to be absent according to the criteria recognized by common medical practices. One particular criteria is established by NCEP-ATP-III.

A "pre-diabetic" subject refers to one whose fasting blood glucose level is in an acceptable range recognized by common medical practices. Although the normal range may depend further on other aspects of the subject, such as age and sex, a fasting blood glucose level in the range of 100 to 125 mg/dl may generally be regarded as "pre-diabetic".

"Active ingredient" refers a component present in the cinnamon extract which renders, directly or indirectly, the intended effect of the cinnamon extract. One particular example is the polyphenol type-A polymer.

Syndrome X is a metabolic condition. It is also interchangeably known as Metabolic Syndrome. As defined by National Cholesterol Education Program's Adult Treatment Panel III (NCEP-ATP-III), Syndrome X represents a collection of risk factors including hypertension, dyslipidemia, obesity, and hyperglycemia. It is noted that not all the risk factors need to be present for a diagnosis of Syndrome X to be made. It is known to the art that a finding of three or more of the following risk factors is indicative of the presence of Syndrome X.

1) Central obesity as measured by waist circumference: Men—greater than 40 inches; Women—greater than 35 inches.
2) Fasting blood triglycerides greater than or equal to 150 mg/dL.
3) Blood HDL (high density lipoprotein) cholesterol: Men—less than 40 mg/dL; Women—less than 50 mg/dL.
4) Blood pressure greater than or equal to 130/85 mmHg.
5) Fasting glucose greater than or equal to 110 mg/dL.

Modern pharmaceutical research has made it almost a certainty to locate a separate, medicinal therapy per each risk factor; a therapy based upon a combination of drugs aimed to target three or more risk factors may bring many unnecessary side effects, let alone unexpected molecular interactions. Therefore, it would be desirable to have a method and a composition based upon a single agent which is active to improve glucose tolerance, enhance lipid profile, decrease blood pressure and otherwise treat Syndrome X.

The role of cinnamon on serum glucose control has been shown in several in vitro studies. For example, an aqueous extract of cinnamon increased glucose metabolism roughly 20-fold in epididymal fat cells (Anderson et al., An improved assay for biologically active chromium; J. Agric. Food Chem. 1978:26:1219-21). More recently, cinnamon supplement was found to improve both glucose and lipid profile in diabetic patients (Khan et al.).

However, there is no teaching in the art that cinnamon by itself, its extract, or combinations with other herbal additives, functions to eliminate one or more risk factors associated with Syndrome X. Further, although prior art documents indicate the role of cinnamon in blood glucose control by being a strong potentiator of insulin, no teaching is made to differentiate the effect of cinnamon based on the pathological conditions of the subjects being treated, such as whether the subjects are non-diabetic or diabetic. A reduction in fasting blood glucose level in a subject may have different clinical implication if the reduction is accompanied by a reversal of diabetic state to non-diabetic state. Hence, it would also be desirable to use a composition containing the cinnamon extract and a method thereof to eliminate at least one of the risk factor associated with Syndrome X. Additionally, it would further be desirable to use a composition containing the cinnamon extract and a method thereof to concurrently reduce and improve three or more of the risk factors associated with Syndrome X.

An herb granted GRAS (Generally Recognized As Safe) status by the United States Food and Drug Administration, cinnamon contains over one hundred different chalcones within it. Chalcones are a type of polyphenol or flavonoid. An extract of cinnamon potentates active ingredients by converting them into a more concentrated form. The isolation of chalcones or other polyphenol molecules from cinnamon follows the general process of aqueous extraction followed by centrifugation to remove non-soluble residues.

Cinnamon may be obtained from various resources. In one particular instance, an extract of cinnamon is derived from the bark of the *Cinnamomum zeylanicum* tree of the genus *Lauraceae*. This tree is native to eastern and southeastern Asia. Other sources of cinnamon may also be used in the methods and materials disclosed herein.

Cinnamon bark may be used in the form of raw bark, sliced, or minced bark, or pulverized bark for the preparation of the therapeutic materials, and pulverized cinnamon bark is used in particular instances.

Extraction and Drying Method

Extracts may be prepared by various methods. Extraction parameters such as water quality, heating temperature, drying temperature, heating time, drying time, and filtering processes all contribute to the quality and efficiency of the process. Water quality directly affects the concentration of active compounds. Poor quality water may cause polyphenols to become decomposed and oxidized during the extraction process. This often results in cinnamon extract powder being reddish in color and the percent concentration of polyphenols being low. Heating time determines the ratio of various polymers being extracted. Heating time also affects the thickness of extraction mixture which then has a direct impact on the downstream filtering process. The temperature of the extraction also affects the level of active polyphenols. In some embodiments the extraction temperature is between 50° C. and 100° C. Optionally, the extractions temperature is between 50° C. and 95° C. Optionally, the temperature is between 50° C. and 90° C. Optionally the extraction temperature is between 50° C. and 90° C. Lastly, drying temperature may vary from 75° C. to 120° C. depending on what other extraction parameters are also used. The amount of solvent used is generally from 2 to 100 times the raw extract material on a weight basis. Illustratively, when 50 g of cinnamon bark is used, the extraction is performed with 1000 ml of water (1 g/m$^1$ is weight of water—i.e. 20 times volume).

Extraction time is also important for obtaining the desired amount of type-A polyphenols. Extractions are optionally performed by heating the raw material in an extraction solvent in excess of 10 minutes, optionally, in excess of 1 hour, optionally between 1 and 3 hours with any subdivision also operable.

Extraction solvents are optionally aqueous or organic. Distilled water or alcohols such as ethanol are optionally used alone or in combination as extraction solvents. The extracts obtained are optionally water soluble.

Illustrative examples of cinnamon extracts are found in U.S. Pat. No. 6,200,569, the contents of which are incorporated herein by reference.

In one embodiment, 50 g clean cinnamon bark is ground into small particles or powder. The powder or particles are mixed with 1000 ml distilled water in a suitable flask. In this and other examples, an amount of buffer is optionally added to maintain the pH of the extraction solvent. The mixture is let stand at room temperature for about 0.5 hour. Additional water may be added is in the range of 1:20 to 1:2000. Too little water may render the mixture too thick for extraction. However, too much water increases drying time. Then the water mixture is heated while being stirred through the use of a magnetic heat stirrer. The temperature and extraction time are crucial to the concentration efficiency of the bioactive polymers. The extraction process is optionally no longer than one hour. Optionally, the ground bark is heated to 100° C. for 15-20 minutes and then simmered for 20-30 minutes while stirring constantly. The boiling time is typically controlled at about 20-25 minutes following heating. The mixture is cooled and stored at 4° C. overnight. An exemplary cinnamon extract obtained by a water extraction is sold as Cinnulin PF by Integrity Nutraceuticals (Spring Hill, Tenn.).

In other embodiments, type A polyphenols are extracted from cinnamon using the following process: 5 g cinnamon and 100 ml 0.1 N acetic acid are combined and autoclaved for 15 minutes. The resultant mixture is cooled, then centrifuged and the precipitate discarded. Four volumes of ethanol/0.1 N acetic acid are added to the supernatant and the mixture is stored overnight at 4° C. The mixture is screened through a filter. To determine the amount of bioactive polymers the mixture is introduced onto an LH-20 column and washed with 600 ml ethanol/0.1 N acetic acid. The desired fraction is then eluted with a 1:1 mixture of acetonitrile and 0.2 N acetic acid. The eluant is then concentrated and introduced onto a HPLC column at 275 nm.

In other embodiments, the initial extraction is performed in the absence of acid. 50 g clean cinnamon bark is ground into small particles or powder and mixed with 1000 ml distilled water/10% ethanol in a suitable flask. Then the water mixture is heated while being stirred through the use of a magnetic heat stirrer. The extraction process is optionally no longer than one hour. Optionally, the ground bark in extraction solvent is heated to a boil for 15-20 minutes, and then simmered for 20-30 minutes while stirring constantly. The boiling time is typically controlled at about 20-25 minutes following heating. The mixture is cooled and stored at 4° C. overnight. It is appreciated that alcohols other than or in addition to ethanol, illustratively methanol, may be used in the extraction procedure as well. When alcohol is used in the extraction solvent is it generally present at 50% or less.

In other embodiments, any one of the extraction solutions (or combinations thereof) described herein is filtered through a filter paper to remove any solid debris. If the solution is too thick for the filter paper, the removal of solids from the solution is optionally done with the use of centrifugation. The resulting supernatant is filtered through medium speed filter paper. The resulting solids are optionally dissolved in 200 mL distilled water, or water/ethanol for a second extraction. The liquid solution containing the solids is mixed and heated for 30 minutes at 80-90° C. and then is filtered to produce a second extraction solution.

In another specific embodiment, the extraction solution(s) are optionally combined together, or used alone and poured onto nonstick tray and allowed to dry at 80-90° C. Vacuumspray dry equipment is optionally used for the drying procedure. The resulting dry cinnamon extract powder is weighed. An extraction ratio is calculated as w/20×100% with was the weight (g) of the dry cinnamon powder. The sample and water ratio, heat time, volume of water in the second extraction may vary depending on the amount of the raw material used for extraction.

In another procedure, HPLC is employed to analyze the effect on the concentrations of the polymers by changes in heating temperature and extraction time. 100 mg dry cinnamon powder is dissolved with 100 ml water or water/ethanol in a flask. The solution is sonicated for 30-45 minutes and filtered through 0.45 uM PTFE syringe. The samples are prepared and tested at different temperatures as follows: samples are extracted at 50-60° C. for one hour, polymers eluting at 17 and 21 minutes seem to have reasonable concentrations. After increasing the temperature to 75-82° C. for 1 hour, the peaks eluting at 17 and 21 minutes are decreased by 2-3%. There are additional two relatively small peaks that seem to surface during this extraction. They elute at 28.5 minutes, 33.5 minutes respectively. After the heating temperature is increased to 85-90° C. for an additional 1 hour, the peaks eluting at 17 and 21 minutes are decreased about 7-9%. The peaks at 28.5 and 33.5 increase significantly. Lastly, the heating temperature is increased to 95-100° C. for 20 minutes and then reduced to 85-95° C. for an additional 40 minutes. The peaks eluting at 17 and 21 minutes seem to decrease by 15-20%. The peaks eluting at 28.5 and 33.5 minutes increase by more than double. According to these results, the polymers at 17 and 21 minutes are converted to isomers at 28.5 and 33.5 minutes respectively. These results suggest that the extraction at 100° C. is preferably suitable to yield acceptable concentration of polymers.

In another procedure, the stabilization of the polymers is analyzed. Various extraction periods at heating temperature of 95-100° C. are tested. After samples are extracted at 95-100° C. for one hour, polymer eluting at 17 and 21 minutes seem to have reasonable concentrations. The peaks eluting at 17 and 21 minutes decrease as the heating temperature increase in the first 2-3 hours. After 3 hours, the peaks eluting at 17 and 21 minutes no longer change as significantly and seem to reach a plateau period. These results suggest that after preferably 3 hour extraction time at temperature of 95-100° C., polymers are stabilized.

Not only is it important to note that the time and temperature play a key factor in sustaining higher concentrations of these key actives, additionally the species of choice can have a dramatic impact on the levels of these Type-A polymers. After thorough review of the world's many species of cinnamon, the following has proven to provide the highest level of active Type-A polymers: *Cinnamomum Burmannii* (Nees) Blume—Microbial Identification Index (MIDI) class; Korintji Cassia.

Cinnamon Extract Containing Bioactive Polymers with Amount Predetermined

The cinnamon extract has a utility to reduce, alleviate, or remedy two or more disorders in a subject categorized as having Syndrome X according to the criteria set forth by NCEP-ATP-III. The disorders manageable by the cinnamon extract formulation include, but are not limited to, abnormalities in FBG, BMI, SBP, HDL, LDL, triglycerides, oxidative stress, and inflammatory state. The cinnamon extract is also used to synergistically increase lean body mass, decrease FBG, and decrease SBP of the subject.

One feature of the cinnamon extract formulation is that its utility to reduce, alleviate, or remedy disorders is not necessarily dependent upon the subjects being diabetic, but instead it exerts its effects on pre-diabetic and other non-diabetic subjects. Therefore prior art documents on the use of raw cinnamon powder to decrease FBG in diabetic patients (type II diabetes), such as those disclosed by Khan et al., and Mang et al., does not teach or suggest treatment of pathological states associated with Syndrome X in non-diabetic subjects.

Cinnamon extract dry power prepared as discussed herein is tested to confirm the presence of certain amount of double-linked polyphenol type-A polymers, singly-linked polymers, or other bioactive polymers through the use of HPLC. This allows for standardization of the extract.

In particular instances, the dry weight of the cinnamon extract powder can be standardized on the basis of a bioactive component, such as the doubly-linked polyphenol type-A polymers. The amount of polyphenol type-A polymers or the like is optionally at or in excess of 1%, is in the range of 0.5% to 25%, optionally 1% to 10%.

In one experimental series, an extract was prepared according to the foregoing procedures using a water extraction solvent. The concentration of the sample was approximately 5.17 mg/ml. It is also very important to note that the concentrations of the polymers change with the temperature and extraction time.

In some embodiments, samples are extracted at 50-60° C. for about one hour, polymers eluting at 17 and 21 minutes have reasonable concentrations. After increasing the temperature to 75-82° C. for one hour, the peaks eluting at 17 and 21 minutes decrease by about 2-3%. There are an additional two relatively small peaks that surface during this extraction. They elute at 28.5 minutes and 33.5 minutes, respectively. After increasing the heat to 85-90° C. for an additional hour, the peaks eluting at 17 and 21 minutes decrease about 7-9%. The peaks at 28.5 and 33.5 minutes increase significantly. Finally, the temperature is increased to 95-100° C. for 20 minutes, and heat was then reduced to 85-95° C. for an additional 40 minutes. The results in peaks eluting 17 and 21 minutes seemed to decrease about 15-20%. The peaks eluting at 28.5 and 33.5 minutes increase more than double from the previous. According to these results, the polyphenols at 17 and 21 minutes are believed to convert to isomers at 28.5 and 33.5 minutes respectively. These results suggest that the extraction at 100° C. seemed to yield the highest concentration of polymers.

An additional experiment is performed on the extract at 100° C. to verify stability. Samples are extracted at 95-100° C. for about one hour, polymers eluting at 17 and 21 minutes seemed to have reasonable concentrations. The peaks eluting at 17 and 21 minutes decrease as the temperature increases in the first 2-3 hours. After 3 hours, the peaks eluting at 17 and 21 minutes do not change significantly. The peak area at 28.5 and 33.5 minutes increases with temperature in the first 2-3 hours. After 3 hours the peaks eluting at 28.5 and 33.5 minutes do not change significantly. These results suggest after 3 hours, these polymers seem to stabilize.

Not only is it important to note that the time and temperature play a key factor in sustaining higher concentrations of these key actives, additionally the species of choice can impact on the levels of these Type-A polymers. The following species appear to provide the highest level of active Type-A polymers: *Cinnamomum Burmannii* (Nees) Blume—Microbial Identification I (MIDI) class; Korintji Cassia. Concentrations of the bioactive polymers appear to be much higher in Indonesian cinnamon versus several other samples.

It has been found that the cinnamon extract is effective in activating glycogen synthase, in stimulating glucose uptake, and in inhibiting glycogen synthase, in increasing total energy intake, and in providing antioxidant effects, collectively leads to increases in lean body mass in the subject receiving cinnamon extract supplement.

Depending on the intended mode of administration, the cinnamon extract supplement can be in pharmaceutical compositions in the form of solid, semi-solid or liquid dosage forms, such as, for example, tablets, suppositories, pills, capsules, powders, liquids, or suspensions, and may be provided in unit dosages suitable for a single administration. Time release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy (20$^{th}$ Edition).

For oral administration, fine powders or granules may contain diluting, dispersing, and/or surface active agents, and may be presented in water or in a syrup, in capsules or sachets in the dry state or in a nonaqueous solution or suspension wherein suspending agents may be included, in tablets wherein binders and lubricants may be included, or in a suspension. Where desirable or necessary, flavoring, preserving, suspending, thickening, or emulsifying agents may be included. Tablets and granules are preferred oral administration forms, and these may be coated.

The cinnamon extract supplement according to the present invention is optionally combined with one or more other components. Such components include, but are not limited to, vitamins (such as vitamin A, vitamin B, vitamin C, vitamin D, or vitamin E), a glucose lowering agent (such as glucose receptor stimulator, insulin sensitizer, glucogen synthesis stimulator, glucose uptake facilitator), a blood pressure lowering agent (such as α-blocker, β-blocker, angiotensi II receptor antagonist), green tea polyphenols (such as epigallocatechin gallate), lipid lowering agent (such as cholesterol synthesis inhibitor).

The cinnamon extract supplement according to the present invention is available as an oral pharmaceutical taken in a form such as tablets, granules, pills, powders, capsules, chewables, or liquid medicinal drinks.

The cinnamon extract supplement according to the present invention is available as a food additive thereto. Examples include foods in a liquid, semi-liquid, solid, paste, or jelly form.

Alleviating Risk Factors Associated with Syndrome X Using Cinnamon Extract Supplement One of the risk factors associated with Syndrome X, hyperglycemia, may be associated with insulin resistance, poor nutritional and exercise habits. Prolonged insulin resistance may eventually develop into diabetes mellitus (DM), which occurs often much later in life. The duration and magnitude of the hyperglycemia may vary. It is well known in the art that vitamins, antioxidants minerals, herbals and nutraceuticals have glucose lowering effects in humans. To name a few, these are vitamin E derivatives, alpha lipoic acid, vitamin C, vanadate, glutathione, etc.

Hypertension is a risk factor which is a significant and powerful contributing component of Syndrome X. Hypertension is defined as a systolic blood pressure (SBP)>140 mmHg and a diastolic blood pressure (DBP)>90 mmHg or >130/80 mmHg in subjects with Syndrome X. Hypertension increases the risk of atherosclerosis, peripheral arterial disease, chronic renal insufficiency, chronic renal failure, dementia and cardiovascular mortality. Hypertension may also find its association with prolonged insulin resistance. In fact, insulin resistance often precedes hypertension by 10-20 years. Insulin resistance-induced hypertension may involve the interplay of nitric oxide, MAPK pathway, and PI3K pathway. On the other hand, vascular inflammatory events also contribute to hypertension. Loss of arterial compliance, distensibility and elastic modulus due to increased collagen and extracellular matrix lay the foundation for the occurrence of hypertension. Hypertensive patients with Syndrome X often require three to four antihypertensive medications to reach a blood pressure of 140/90 mmHg or less. Lower recommended target blood pressure goals of 130/80 mmHg or perhaps 110/70 mmHg cannot be achieved without aggressive use of balanced drug and non-drug treatments.

Yet another underlying etiology of Syndrome X, dyslipidemia, is characterized as a collection of phenotypes that includes increase free fatty acids, elevated serum triglycerides, decreased HDL cholesterol, elevated LDL cholesterol. Low HDL cholesterol, with a shift to smaller size HDL, is common in Syndrome X and is due to triglyceride enrichment of HDL, increased HDL degradation by hepatic lipase and increased apolipoprotein A1 catabolism. A therapeutic strategy for dyslipidemia treatment should be to reduce LDL cholesterol to 60-70 mg/dL, increase HDL cholesterol to 40 mg/dL in men and 50 mg/dL in women, and to reduce triglyceride levels to less than 150 mg/dL. Appropriate combinations of nutritional supplements and lipid lowering drugs may work in concert to help achieve these goals. It is known in the art that dietary supplements helpful in reducing dyslipidemia associated symptoms include niacin, marine lipids, policosanol, plant sterols, soy, green tea, flax, tocotrienols, pantothenic acid, etc.

One or more risk factors are represented in each underlying etiology associated with Syndrome X. These risk factors include, but are not limited to, abnormalities in systolic blood pressure (SBP), in fasting blood glucose (FBG), in body mass index (BMI), in high-density lipoprotein cholesterol, low-density lipoprotein cholesterol, serum triglycerides, etc. Conventionally, according to National Cholesterol Education Program's Adult Treatment Panel III, concurrent occurrences in abnormal SBP, FBG, and BMI are indicative of a finding of Syndrome X in an individual. An abnormal SBP, FBG, or BMI in the individual is defined as a value of SBP>=130 mmHg, of FBG>=110 mg/dL.

Cinnamon extract materials are metabolized in the individual to yield a therapeutically effect amount of compound species, namely cinnamon polyphenol, cinnamon oligomer, cinnamon catechin or epicatechin, cinnamon chalcone, and cinnamon MHCP. MHCP has been discovered to stimulate glucose uptake by facilitating glycogen production. In particular therapies, each dose of the cinnamon extract supplement is selected so as to deliver into the individual MHCP in the amount of 10-30 milligrams (mg). A method of treatment includes administering a therapeutically effective amount of an inventive cinnamon extract supplement to an individual with a manifestation of Syndrome X.

Variable dosing regiments are operative in the method of treatment. While in some instances, a single dose treatment is effective in producing therapeutic effects, in other instances a treatment period in the range of 6 weeks to 3 months is utilized.

The supplement can be administered orally; parentally, such as intravenously; by intramuscular injection; by intraperitoneal injection; or transdermally. The exact dose of the supplement required can vary from subject to subject, depending on the age, weight, general condition of the subject, the severity of risk factors associated with Syndrome X, the mode of administration, and the like. An appropriate dose is readily determined by one of ordinary skills in the art using only routine experimentation given the teachings herein. Generally, dosage is in the range of 10-1,000 mg of equivalent of dry cinnamon powder per day.

Parenteral administration is generally by injection. Injectables can be prepared in conventional forms, either liquid solutions or suspensions, solid forms suitable for solution or prior to injection, or as suspension in liquid prior to injection or as emulsions.

The example presented below is intended to illustrate a particular embodiment of the invention and is not intended to limit the scope of the specification, including the claims, in any way.

EXAMPLE

The effect of supplementation with a water-soluble cinnamon extract (Cinnulin PF™) on features of Syndrome X.

Experiment Design

This study was a randomized, placebo-controlled, double-blind clinical trial with two parallel groups. Serum chemistry, body weight, and body composition were measured at baseline and at the end of the 12-week supplementation period. Subjects also completed 3-day food records and had measurements of their systolic and diastolic blood pressures during pre (week 0), mid (week 6), and post (week 12) testing. FIG. 1 presents the flow of participants through the study.

i) Subjects

Subjects were recruited from northeastern Ohio, a typical suburban region, by word of mouth and posted announcements. Thirty (30) potential participants aged 30-60 years were interviewed by telephone. Of these, 22 were invited for a preliminary screening consisting of height, weight, blood pressure, and a fasting blood sample. Subjects were required to have FBG between 100 mg/dL (5.6 mmol/L) and 125 mg/dL (6.9 mmol/L), have normal values for liver and kidney function tests, and be willing to maintain their usual dietary and physical activity habits. Subjects were excluded from the study if they had a body mass index (BMI)>40 kg/m$^2$, thyroid disease, hypogonadism, a history of musculoskeletal, autoimmune, or neurologic disease, or if they were currently taking thyroid, hyperlipidemic, hypoglycemic, anti-hypertensive, or anti-coagulant medications. Prior to obtaining written, informed consent from each subject, an institutional review board (IntegReview Inc, Austin, Tex.) approved the experimental protocol. All procedures in the study were in accord with ethical standards set forth in the Helsinki Declaration of 1975 as revised in 1983.

ii) Supplementation

After matching for age, FBG, SBP, and habitual physical activity levels, subjects were assigned to a cinnamon water extract material (Cinnulin PF®) (n=12) or placebo (n=10) group. Each subject was instructed to take two capsules (250 mg) of their respective supplement twice per day (with breakfast and dinner). According to the manufacturer, 500 mg of Cinnulin PF® is equivalent to approximately 10 g of whole cinnamon powder (i.e., 20:1 extract), and contains at least 1% doubly-linked polyphenol type-A polymers (considered to be the bioactive component), and <0.001% coumaric acid and cinnamaldehyde. Supplements were prepared in a 2-piece hard shell capsule form and packaged in coded generic containers for double-blind administration by Integrity Nutraceuticals International (Sarasota, Fla.). Medical monitoring and compliance to the supplementation protocol was supervised by a research technician who contacted the subjects on a weekly basis. Each subject was required to return the original bottle of their respective supplement for pill counts during mid (week 6) and post (week 12) testing.

A second group is supplemented with a water/ethanol cinnamon extract. As this extract has similar polyphenol levels as the water extract, the dosing is the same as for the water extract.

Heart Rate and Blood Pressure

All subjects reported to the laboratory after a 12-hour fast and at least 48 hours after participating in intense physical activity. Following ten minutes of seated rest, subjects' heart rate and blood pressure were determined by palpation of the radial artery and aneroid sphygmomanometry, respectively. The same technician performed all measurements using standard procedures.

iii) Blood Collection And Analyses

Immediately following blood pressure readings, approximately 20 mL (~4 teaspoons) of blood was drawn with stasis via venipuncture of an antecubital vein. All blood samples were taken in the morning at approximately the same time of day to minimize diurnal variation, and subjects used their baseline diet records to standardize their final (evening) meal before mid (week 6) and post (week 12) testing.

Blood samples were harvested into tubes with and without EDTA, centrifuged (Drucker model 614, Philipsburg, Pa.) at room temperature for 15 minutes at 1200×g to obtain plasma and serum, and immediately placed into two aliquots. One aliquot was immediately analyzed for a 21-item clinical chemistry profile (Hitachi D2400, Roche Diagnostics, Germany) by a certified clinical laboratory (Laboratory Corporation of America, Dublin, Ohio). This profile consisted of a comprehensive metabolic panel (glucose, BUN, creatinine, sodium, potassium, chloride, carbon dioxide, calcium, total protein, albumin, globulin, total bilirubin, alkaline phosphatase, AST [SGOT], and ALT [SGPT]) as well as a lipid profile (total cholesterol, HDL-C, LDL-C, VLDL-C, triacylglycerol).

Plasma and erythrocyte pellets were immediately isolated from the second aliquot and were stored at −80° C. until additional measurements were made by the Nutrients Requirements and Functions Laboratory in Beltsville, Md. These measurements included: erythrocyte Cu—Zn superoxide dismutase (SOD) activity, erythrocyte glutathione peroxidase (GSH-Px) activity, plasma thiols, plasma malondialdehyde (MDA), and ferric reducing activity of plasma (FRAP).

iv) Body Composition

Body weight was measured using a calibrated digital A&D™ Medical Scale (model UC-300, Milpitas, Calif.), standing height was measured using a wall-mounted stadiometer (Seca model 216, Hanover, Md.) and body composition was measured with dual-energy x-ray absorptiometry (GE Lunar DPX Pro, Madison, Wis.). All dual-energy x-ray absorptiometry (DEXA) scans were performed by the same technician and analyzed according to software (enCORE version 7.53.002, 2003) provided by the manufacturer. Briefly, subjects were positioned in the scanner according to standard procedures and remained motionless for approximately 15 minutes during scanning. DEXA segments for the arms, legs, and trunk were subsequently obtained using standard anatomical landmarks. Using a three-compartment model, DEXA calculates fat mass, lean mass, and bone mass. Percent fat was calculated by dividing fat mass by the total scanned mass. Quality control calibration procedures were performed prior to all scans using a calibration block provided by the manufacturer. Prior to this study, reliability was determined via intra-class correlation coefficients for repeated DEXA measurements of lean mass, bone mineral content, and fat mass to be >0.98.

v) Diet and Physical Activity

As mentioned previously, this study used a free-living design where subjects were advised to maintain their normal diet during the study. To verify this, subjects completed 3-d food records (which included two weekdays and one weekend day) during baseline testing, week 6, and week 12. All food records were analyzed by a licensed, registered dietitian using commercially available software (NutriBase IV Clinical Edition, AZ). To enhance accuracy of the food records, all subjects received instruction during baseline testing on how to accurately estimate portion sizes. This counseling was reinforced during each visit to the laboratory. No dietary supplements were allowed with the exception of standard strength multivitamins.

Subjects were also advised to maintain their current level of habitual physical activity throughout the study. Physical activity levels were measured with the Framingham Physical Activity Index (Kannel W B, Sorlie P. Some health benefits of physical activity: The Framingham Heart Study. Arch. Intern. Med. 1979, 139:857-861) during baseline testing, week 6, and week 12.

vi) Statistical Analyses

Statistical analyses were conducted using Statistica version 7.1 (Stat Soft Inc., Tulsa, Okla.). Differences between groups at baseline were analyzed with independent t-tests and chi-square tests. Separate 2×2 or 2×3 (Group×Time) univariate ANOVA with repeated measures on the last factor were used to analyze between group differences over time. Since a drop out did occur in this study, intent-to-treat analyses (ITT) were performed, using the last-observation-carried-forward method. In an ITT approach, all randomized subjects' data are included in the data analysis, regardless of whether they complete the trial or are compliant with the procedures. In contrast, most studies on dietary supplements use a "per protocol" analysis and exclude noncompliant subjects or subjects who drop out. Although a discussion of ITT analyses is beyond the scope of this discussion, many researchers consider ITT to be the preferred method of data analysis in clinical efficacy studies as it is less prone to bias. When a significant interaction was observed, Fisher's Least Significant Differences (LSD) post-hoc test was performed. When the interaction term was "marginally significant" (i.e., 0.05<P<0.10), changes from day 0 to day 84 within treatment groups were assessed with a paired t-test. Differences were considered statistically significant at P<0.05. Power analysis for this 2×3 design indicated that a sample size of 10-15 subjects per group yields moderate power 0.80) for delta values of 0.75 to 1.25.

Results

Table 1 presents baseline characteristics of the subjects. Both groups met the criteria of the Adult Treatment Panel III of the National Cholesterol Education Program for having the metabolic syndrome. Specifically, both groups had FBG>110 mg/dL (Cinnulin: 116±13, Placebo: 112±10), systolic BP>130 mm Hg (Cinnulin: 133±14, Placebo: 133±22) and triacylglycerol>150 mg/dL (Cinnulin: 166±142, Placebo: 165±107). There were no significant differences in general, metabolic, or dietary characteristics between groups at baseline.

TABLE 1

Baseline Characteristics of the Subjects Recruited for the Study

| Parameters Tested | Placebo (n = 10) | Cinnulin (n = 12) | P-value |
|---|---|---|---|
| General | | | |
| Sex (M/F) | 3/7 | 8/4 | 0.15 |
| Age (y) | 45.6 ± 11.1 | 46.3 ± 8.8 | 0.88 |
| Weight (kg) | 89.3 ± 30.6 | 93.1 ± 18.1 | 0.72 |
| BMI (kg/m$^2$) | 34.4 ± 12.6 | 32.3 ± 5.7 | 0.61 |
| Body Fat (%) | 43.8 ± 8.0 | 37.9 ± 9.2 | 0.13 |
| Lean Mass (kg) | 43.9 ± 11.1 | 53.7 ± 11.8 | 0.06 |
| Metabolic | | | |
| Systolic Blood Pressure (mm Hg) | 133 ± 22 | 133 ± 14 | 0.94 |
| Diastolic Blood Pressure (mm Hg) | 83 ± 14 | 83 ± 6 | 0.94 |
| Glucose (mg/dL) | 112 ± 10 | 116 ± 13 | 0.40 |
| Total Cholesterol (mg/dL) | 192 ± 49 | 185 ± 44 | 0.72 |
| LDL Cholesterol (mg/dL) | 105 ± 52 | 107 ± 36 | 0.90 |
| VLDL Cholesterol (mg/dL) | 33 ± 21 | 25 ± 9 | 0.28 |
| HDL Cholesterol (mg/dL) | 55 ± 14 | 50 ± 13 | 0.36 |
| Triacylglycerol (mg/dL) | 165 ± 107 | 166 ± 142 | 0.99 |
| Dietary | | | |
| Kcals/day | 1706 ± 427 | 1741 ± 551 | 0.87 |
| % Carbohydrate | 46 ± 13 | 43 ± 12 | 0.59 |
| % Fat | 33 ± 9 | 33 ± 10 | 0.98 |
| % Protein | 20 ± 11 | 23 ± 7 | 0.38 |
| Fiber (grams/d) | 14 ± 7 | 16 ± 8 | 0.42 | i) Supplementation Compliance and Adverse Events.

Compliance to the supplementation regimen was defined as the number of capsules actually taken by each subject divided by the number of capsules that should have been taken over the course of the study. Excluding one drop out in the Cinnulin group, compliance was >97% in both groups. Adverse events were based on spontaneous reporting by subjects as well as open-ended inquiries by members of the research staff. No adverse events were reported during the study in either group.

ii) HR and BP.

After 12-weeks, subjects in the Cinnulin group decreased their SBP by 3.8% (from 133±14 mm Hg [pre] to 128±18 mm Hg [post], P<0.001) compared to subjects in the Placebo group (from 133±22 mm Hg [pre] to 142±20 mm Hg [post]). No between or within-group changes in diastolic blood pressure (Cinnulin: from 83±6 mm Hg [pre] to 84±9 mm Hg [post]; Placebo: from 83±14 mm Hg [pre] to 86±12 mm Hg [post], P<0.32) or HR (Cinnulin: from 69±14 beats/min [pre] to 69±12 beats/min [post]; Placebo: from 71±15 beats/min [pre] to 74±8 beats/min [post], P<0.73) were noted in either group.

iii) Blood Chemistry.

Figure 2:
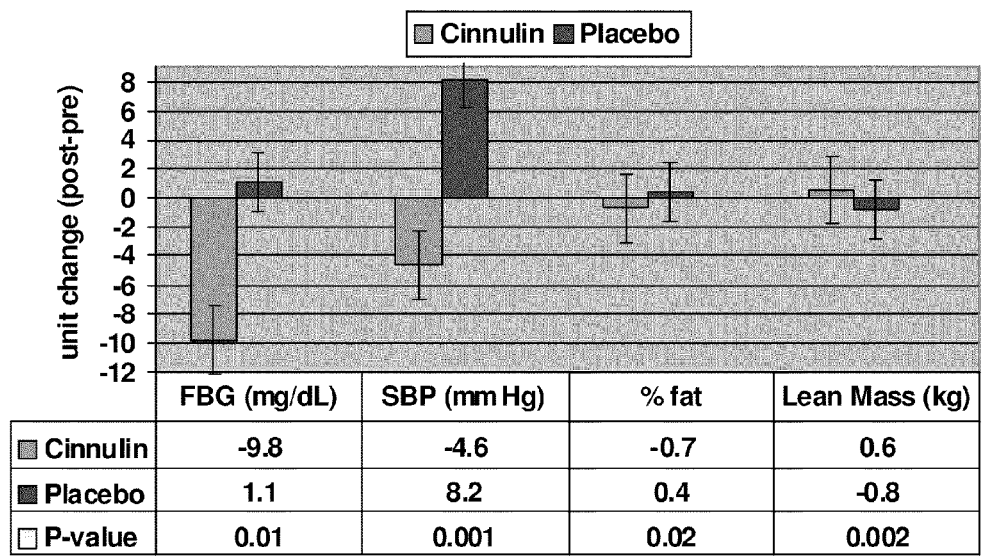
FIG. 2 shows the significance of FBG, SBP, % fat and lean mass changes elicited from subjects who have been supplemented with the water-soluble cinnamon extract.

FIG. 2 presents changes in FBG during the study. Subjects in the Cinnulin group had significant decreases in FBG (−8.4%: from 116.3±12.8 mg/dL [pre] to 106.5±20.1 mg/dL [post], P<0.01) compared to subjects in the Placebo group (from 112.0±10.0 mg/dL [pre] to 113.1±14.7 mg/dL [post]). No other between group effects were noted for BUN, creatinine, bilirubin, alkaline phosphatase, AST (SGOT), ALT (SGPT), sodium, potassium, chloride, calcium, albumin, globulin, $CO_2$, total protein, total cholesterol, HDL-C, LDL-C, VLDL-C, or triglycerides and all values remained within normal clinical limits (Table 2). Subjects taking the water/ethanol extract have similar blood chemistries.

TABLE 2

Selected Hematological Responses to Supplementation.

| | Placebo (n = 10) | Cinnulin (n = 12) | P-value (GxT) | Reference Interval |
|---|---|---|---|---|
| BUN: Creatinine | | | 0.21 | 8-27 |
| Pre | 16 ± 5 | 16 ± 4 | | |
| Mid | 19 ± 5 | 18 ± 4 | | |
| Post | 16 ± 4 | 18 ± 4 | | |
| Bilirubin (mg/dL) | | | 0.50 | 0.1-1.2 |
| Pre | 0.5 ± 0.1 | 0.7 ± 0.3 | | |
| Mid | 0.5 ± 0.1 | 0.8 ± 0.4 | | |
| Post | 0.5 ± 0.2 | 0.6 ± 0.3 | | |
| Alkaline Phosphatase (IU/L) | | | 0.12 | 25-150 |
| Pre | 77 ± 17 | 65 ± 14 | | |
| Mid | 71 ± 16 | 67 ± 16 | | |
| Post | 67 ± 16 | 60 ± 11 | | |
| Aspartate aminotransferase (IU/L) | | | 0.94 | 0-40 |
| Pre | 29 ± 15 | 29 ± 17 | | |
| Mid | 26 ± 11 | 26 ± 13 | | |
| Post | 25 ± 8 | 24 ± 8 | | |
| Alanine aminotransferase (IU/L) | | | 0.59 | 0-40 |
| Pre | 30 ± 16 | 38 ± 28 | | |
| Mid | 30 ± 17 | 34 ± 25 | | |
| Post | 28 ± 14 | 32 ± 22 | | |
| Cholesterol (mg/dL) | | | 0.81 | 100-199 |
| Pre | 192 ± 49 | 185 ± 44 | | |
| Mid | 191 ± 50 | 190 ± 36 | | |
| Post | 193 ± 47 | 190 ± 33 | | |
| Triacylglycerol (mg/dL) | | | 0.75 | 0-149 |
| Pre | 165 ± 107 | 166 ± 142 | | |
| Mid | 172 ± 111 | 152 ± 76 | | |
| Post | 195 ± 146 | 162 ± 132 | | |
| HDL (mg/dL) | | | 0.73 | 40-59 |
| Pre | 55 ± 14 | 50 ± 13 | | |
| Mid | 54 ± 15 | 48 ± 13 | | |
| Post | 55 ± 16 | 50 ± 13 | | |
| VLDL (mg/dL) | | | 0.31 | 5-40 |
| Pre | 33 ± 21 | 25 ± 9 | | |
| Mid | 34 ± 21 | 30 ± 15 | | |
| Post | 36 ± 22 | 25 ± 11 | | |
| LDL (mg/dL) | | | 0.44 | 0-99 |
| Pre | 105 ± 52 | 107 ± 36 | | |
| Mid | 102 ± 57 | 112 ± 34 | | |
| Post | 99 ± 54 | 111 ± 29 | | | iv) Body Composition.

FIG. 2 presents changes in body composition during the study. Subjects in the Cinnulin group increased their lean mass by 1.1% (from 53.7±11.8 kg [pre] to 54.3±11.8 kg [post], P<0.002), and decreased their body fat by 0.7% (from 37.9±9.2% [pre] to 37.2±8.9% [post]; within-group analysis, P<0.02). No changes in lean mass (from 43.9±11.1 kg [pre] to 43.1±10.9 kg [post]) or fat mass (from 43.8±8.0% [pre] to 44.2±9.0% [post]) were noted in the Placebo group. Because the baseline value for lean mass was marginally significant (P<0.06), we also performed an ANCOVA using week 0 lean mass as the covariate. Results confirmed that lean mass at week-12 was significantly greater in the Cinnulin group (P<0.004). Subjects dosed with the water/ethanol cinnamon extract show similar results.

v) Diet and Physical Activity.

Table 3 presents totals for three-day dietary intake obtained during the study. No changes in total daily energy or macronutrient intake were noted during the study, although there was a trend for subjects in the Cinnulin group to consume more total Calories (P<0.07). Follow-up testing for within-group changes (via dependent t-test) indicated subjects in the Cinnulin group ingested significantly more total energy during week-12 (P<0.04). No changes in habitual physical activity occurred between groups over time (data not shown).

TABLE 3

Three-Day Total Dietary Intake of the Subjects

| | Placebo (pre) | Placebo (post) | Cinnulin (pre) | Cinnulin (post) | P-value (GxT) |
|---|---|---|---|---|---|
| Total energy (kcals/d) | 1706 ± 427 | 1613 ± 364 | 1741 ± 551 | 1982 ± 530 | 0.07 |
| Carbohydrate (%) | 46 ± 13 | 46 ± 11 | 43 ± 12 | 43 ± 10 | 0.94 |
| Fat (%) | 33 ± 9 | 33 ± 8 | 33 ± 10 | 35 ± 7 | 0.70 |
| Protein (%) | 20 ± 11 | 20 ± 7 | 23 ± 7 | 21 ± 7 | 0.91 |
| Saturated fat (g/d) | 18 ± 10 | 18 ± 11 | 16 ± 7 | 23 ± 13 | 0.37 |
| Cholesterol (mg/d) | 331 ± 239 | 280 ± 174 | 258 ± 137 | 275 ± 155 | 0.26 |
| Sodium (mg/d) | 3402 ± 1488 | 4160 ± 2098 | 4426 ± 2351 | 4419 ± 1943 | 0.58 |
| Fiber (g/d) | 14 ± 7 | 17 ± 7 | 16 ± 8 | 20 ± 11 | 0.65 |

The foregoing establishes that cinnamon extract materials, including a water extract (Cinnulin PF) and a water/ethanol extract, of the types described herein can treat multiple symptoms associated with Syndrome X.

Any patents or publications mentioned in this specification are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The apparatus and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for reducing systolic blood pressure or body mass index in a subject in need thereof comprising the step of:
   administering to a subject in need thereof wherein said subject has abnormal systolic blood pressure or abnormal body mass index a therapeutically effective amount of a water or water/ethanol extract of cinnamon bark, wherein the water or water/ethanol extract of cinnamon bark comprises at least 1 percent polyphenol type-A polymers; and
   reducing systolic blood pressure or body mass index in said subject by said step of administering, wherein said at least 1 percent of polyphenol type-A polymers in said water or water/ethanol extract is obtained by preparing said water or water/alcohol extract by extraction of *Cinnamomum* sp. in water by a process comprising heating said *Cinnamomum* sp. and said water to about 100 degrees Celsius for 15 to 20 minutes, and subsequently reducing the temperature to about 80-95 degrees Celsius for 20-30 minutes.

2. The method of claim 1, wherein said subject has an abnormal body mass index.

3. The method of claim 1, wherein the therapeutically effective amount of the extract of cinnamon bark is administered orally, intravenously, by intramuscular injection, by intraperitoneal injection, or transdermally.

4. The method of claim 1, wherein the therapeutically effective amount of the extract of cinnamon bark is administered orally in the form selected from the group consisting of tablets, suppositories, pills, capsules, powders, liquids, suspensions.

5. The method of claim 1, wherein the therapeutically effective amount of the extract of cinnamon bark comprises a predetermined amount of polyphenol type-A polymers.

6. A method for reducing systolic blood pressure in a subject in need thereof comprising the step of:
   administering to a subject in need thereof wherein said subject has abnormal systolic blood pressure a therapeutically effective amount of a water soluble water or water/ethanol extract of cinnamon bark, wherein the water or water/ethanol extract of cinnamon bark comprises at least 1 percent polyphenol type-A polymers; and
   reducing systolic blood pressure in said subject by said step of administering.

7. The method of claim 6 wherein said polyphenol type-A polymers are present in an amount from 0.5 to 25 percent.

* * * * *